United States Patent
Abe

(10) Patent No.: US 7,541,511 B2
(45) Date of Patent: Jun. 2, 2009

(54) MOUSE EXHIBITING CHARACTERISTICS OF ROTHMUND-THOMSON SYNDROME AND PREPARATION METHOD THEREOF

(75) Inventor: Masumi Abe, Chiba (JP)

(73) Assignee: National Institute of Radiological Sciences, Chiba (JP)

( * ) Notice: Subject to any disclaimer, the term of this patent is extended or adjusted under 35 U.S.C. 154(b) by 262 days.

(21) Appl. No.: 11/084,955

(22) Filed: Mar. 21, 2005

(65) Prior Publication Data

US 2005/0183149 A1    Aug. 18, 2005

Related U.S. Application Data

(63) Continuation of application No. PCT/JP2004/009380, filed on Jun. 25, 2004.

(30) Foreign Application Priority Data

Jun. 27, 2003    (JP)    ............... 2003-185409

(51) Int. Cl.
*A01K 67/027*    (2006.01)
*C12N 15/00*    (2006.01)

(52) U.S. Cl. ........................... 800/18; 800/22

(58) Field of Classification Search ............... None
See application file for complete search history.

(56) References Cited

OTHER PUBLICATIONS

Lee et al (Molecular and Cellular Biology, 1998, vol. 18, No. 5, p. 3059-3068).*
Sigmund, C.D. 2000. Arterioscler Thromb Vasc Biol.20:1425-1429.*
Wall, R.J. 1996. Theriogenology 45:57-68.*
Mullins et al. (1996, Clin. Invest. vol. 97, No. 7, 1557-1560).*
Campbell and Wilmut (Theriogenology, 1997. vol. 47, No. 1, pp. 63-72).*
Bradley et al. 1992. Biotechnology, vol. 10, pp. 534-539.*
Ohhata et al.; "Cloning, genomic structure and chromosomal localization of the gene encoding mouse DNA helicase RECQL5β," *Elsevier Science B.V.*, Gene 280, 2001, pp. 59-66.
Kitao et al.; "Mutations in RECQL4 cause a subset of cases of Rothmund-Thomson syndrome," *Nature Genetics*, vol. 22, May 1999, pp. 82-84.
Kitao et al.; "Rothmund-Thomson Syndrome Responsible Gene, RECQL4: Genomic Structure and Products," *Genomics*, vol. 61, 1999, pp. 268-276.
Hoki et al.: "Growth retardation and skin abnormalities of the Recq14-deficient mouse," 2003, vol. 12(18), pp. 2293-2299.

* cited by examiner

*Primary Examiner*—Celine X Qian
(74) *Attorney, Agent, or Firm*—Husch Blackwell Sanders Welsh & Katz LLP

(57) ABSTRACT

A non-human mammal, especially a mouse exhibiting a characteristic of Rothmund-Thomson syndrome prepared by introducing a mutation into exon 13 of RECQL4 gene; and method of preparation thereof are provided.

6 Claims, 5 Drawing Sheets

SHORT ARM MCS: Xba I, Pme I, Hpa I, Mlu I, Not I, Sac II

LONG ARM MCS: Hind III, Swa I, Srf I, Hind III, Cla I

PGKNeo
NTBlunt 6450bp
pBluescript
HSV-TK

+/+  +/−  −/−
8kb —
6kb —

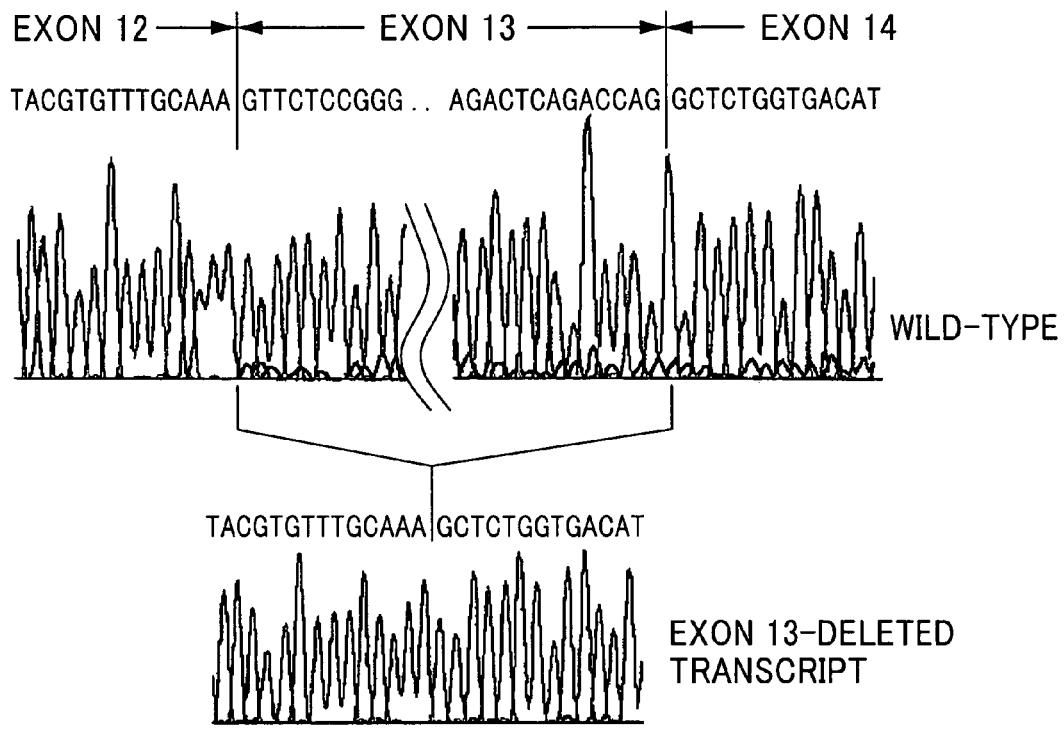
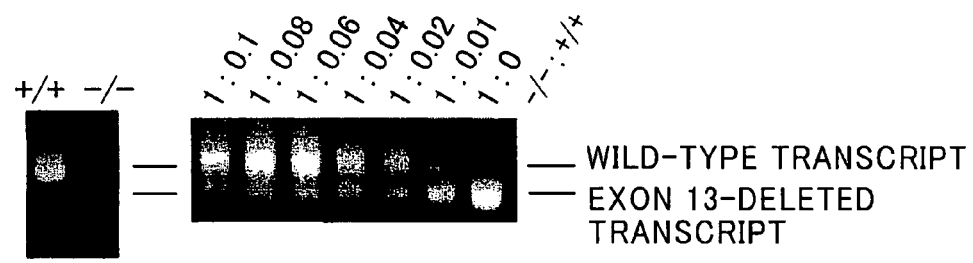

SEQUENCE LISTING

<160> NUMBER OF SEQ ID NOS: 17

<210> SEQ ID NO 1
<211> LENGTH: 3651
<212> TYPE: DNA
<213> ORGANISM: Mus musculus
<220> FEATURE:
<221> NAME/KEY: CDS
<222> LOCATION: (1)..(3648)
<223> OTHER INFORMATION:

<400> SEQUENCE: 1

```
atg gag cgg ctc gcg acc gtt cgc gcg cgg cta cag gag tgg gaa cgc      48
Met Glu Arg Leu Ala Thr Val Arg Ala Arg Leu Gln Glu Trp Glu Arg
1               5                  10                  15 gct ttt gca cgg ctg cac ggg cga cgg cca gcg aag ggg gat gtg gag      96
Ala Phe Ala Arg Leu His Gly Arg Arg Pro Ala Lys Gly Asp Val Glu
            20                  25                  30 gcg gca cct gaa gag acc cgc gcg ctc tac cgt gag tac cgt aac cta     144
Ala Ala Pro Glu Glu Thr Arg Ala Leu Tyr Arg Glu Tyr Arg Asn Leu
        35                  40                  45 aag cag gcg gtg cgt cag gct gac gac aga cat cgt gtc cta gag caa     192
Lys Gln Ala Val Arg Gln Ala Asp Asp Arg His Arg Val Leu Glu Gln
    50                  55                  60 tca ctt gcc gag gca gct gag gag gca cag gag cca agc tgc tgg ggt     240
Ser Leu Ala Glu Ala Ala Glu Glu Ala Gln Glu Pro Ser Cys Trp Gly
65                  70                  75                  80 ccc cac ctg agt cga gct gca acg cag aat acg cag tct atg cca aaa     288
Pro His Leu Ser Arg Ala Ala Thr Gln Asn Thr Gln Ser Met Pro Lys
                85                  90                  95 cag agc cta ctg agt tct gta caa gac tat ggg aag agg ctc aaa gcc     336
Gln Ser Leu Leu Ser Ser Val Gln Asp Tyr Gly Lys Arg Leu Lys Ala
            100                 105                 110 aat ctg aaa aac aca aca cag act gga cca acc cag agc aga aaa ctc     384
Asn Leu Lys Asn Thr Thr Gln Thr Gly Pro Thr Gln Ser Arg Lys Leu
        115                 120                 125 cag ctt cag aag aga tcc ttg tcc aca gtt cct gcc cca agg cca cca     432
Gln Leu Gln Lys Arg Ser Leu Ser Thr Val Pro Ala Pro Arg Pro Pro
    130                 135                 140 ggc tca aag act gaa tcc ccc tgt cca gac gaa gct gac gat gca ctt     480
Gly Ser Lys Thr Glu Ser Pro Cys Pro Asp Glu Ala Asp Asp Ala Leu
145                 150                 155                 160 cct cgg gtt cct gag ccc cgg ccg agg ctg ggc cag ctc cag cag ctc     528
Pro Arg Val Pro Glu Pro Arg Pro Arg Leu Gly Gln Leu Gln Gln Leu
                165                 170                 175 cga tca tcc ctc agc cgg agg ttg act tcc cta gac cct ggt tgg tta     576
Arg Ser Ser Leu Ser Arg Arg Leu Thr Ser Leu Asp Pro Gly Trp Leu
            180                 185                 190 gag agg tgt cac aac aga gtt tca gat ctt cta gag gtt ccg ggt gct     624
Glu Arg Cys His Asn Arg Val Ser Asp Leu Leu Glu Val Pro Gly Ala
        195                 200                 205 tgt ggg ctt gac ctg agt gca gag gag tca cag cct cag atg tca ggc     672
Cys Gly Leu Asp Leu Ser Ala Glu Glu Ser Gln Pro Gln Met Ser Gly
    210                 215                 220 aag gtg aac atc gct gat cct gac atc cag tca gaa gta tct gta cag     720
Lys Val Asn Ile Ala Asp Pro Asp Ile Gln Ser Glu Val Ser Val Gln
225                 230                 235                 240 agc cca gag gcc ata gcc caa cag cca gcc cag gtt ttg tca cag agc     768
Ser Pro Glu Ala Ile Ala Gln Gln Pro Ala Gln Val Leu Ser Gln Ser
                245                 250                 255
```

```
ccc aaa tcc atc aac agt aaa ggc agg aag cgg aag tgg aat gag aag      816
Pro Lys Ser Ile Asn Ser Lys Gly Arg Lys Arg Lys Trp Asn Glu Lys
        260                 265                 270 ggg gag gac ttt gca caa gac cag ccc agc agc gga gca gga ccc ctg      864
Gly Glu Asp Phe Ala Gln Asp Gln Pro Ser Ser Gly Ala Gly Pro Leu
            275                 280                 285 tct gag gga gcc agg gct aca gta cat ggg caa gac cct cca gga gaa      912
Ser Glu Gly Ala Arg Ala Thr Val His Gly Gln Asp Pro Pro Gly Glu
290                 295                 300 ccc aca caa gtg aat gtc cct cag cca tgc aat tcc tca aac cag gcc      960
Pro Thr Gln Val Asn Val Pro Gln Pro Cys Asn Ser Ser Asn Gln Ala
305                 310                 315                 320 agg aca gag aag gct aag ggc aca acc cac ctc cat gcc tct cct cga     1008
Arg Thr Glu Lys Ala Lys Gly Thr Thr His Leu His Ala Ser Pro Arg
                325                 330                 335 cca gct tcc cta gac aga ggg aac tat att cga ctc aac atg aaa aac     1056
Pro Ala Ser Leu Asp Arg Gly Asn Tyr Ile Arg Leu Asn Met Lys Asn
            340                 345                 350 aaa cgc ttt gta cga gtt ggg gcc aat cgg ggc agg ctt ctc cgt aag     1104
Lys Arg Phe Val Arg Val Gly Ala Asn Arg Gly Arg Leu Leu Arg Lys
        355                 360                 365 cag gta tgg aag caa aag tgg aag aag aaa caa gct gcg ttt ggg gga     1152
Gln Val Trp Lys Gln Lys Trp Lys Lys Lys Gln Ala Ala Phe Gly Gly
370                 375                 380 agt gga ccc agg gcc aca gac aag gac act tgt ttc cgg tgt ggg cag     1200
Ser Gly Pro Arg Ala Thr Asp Lys Asp Thr Cys Phe Arg Cys Gly Gln
385                 390                 395                 400 ttt ggt cac tgg gca tcc cag tgt tcc caa cca ggc ccc acc ctg acc     1248
Phe Gly His Trp Ala Ser Gln Cys Ser Gln Pro Gly Pro Thr Leu Thr
                405                 410                 415 gtc caa gag gaa ggt gac agg gat gac aaa cag ccc att tcc acc ttg     1296
Val Gln Glu Glu Gly Asp Arg Asp Asp Lys Gln Pro Ile Ser Thr Leu
            420                 425                 430 gaa gaa gta gca cag agg aca ggc act gct tcc tgt cac cac tct ggt     1344
Glu Glu Val Ala Gln Arg Thr Gly Thr Ala Ser Cys His His Ser Gly
        435                 440                 445 gag gaa aca cag cct gct gcg cca gag cta cag gtg cct cat tgc ccc     1392
Glu Glu Thr Gln Pro Ala Ala Pro Glu Leu Gln Val Pro His Cys Pro
450                 455                 460 acc cca atg tca ccc ctc tac cca ccg gga cct ttg gga caa gta gca     1440
Thr Pro Met Ser Pro Leu Tyr Pro Pro Gly Pro Leu Gly Gln Val Ala
465                 470                 475                 480 gaa acc cct gct gaa gta ttc cag gcc cta gag cgg cta ggg tac cga     1488
Glu Thr Pro Ala Glu Val Phe Gln Ala Leu Glu Arg Leu Gly Tyr Arg
                485                 490                 495 gcc ttc cgc cct ggg caa gag cgt gca atc atg cgg att ctt tct ggc     1536
Ala Phe Arg Pro Gly Gln Glu Arg Ala Ile Met Arg Ile Leu Ser Gly
            500                 505                 510 atc tct act ctg tta gtg ttg ccc acg ggt gct gga aag tct ctg tgc     1584
Ile Ser Thr Leu Leu Val Leu Pro Thr Gly Ala Gly Lys Ser Leu Cys
        515                 520                 525 tac cag ctt cct gca ctg ctc tat gcc cag cga agc ccc tgc ctc aca     1632
Tyr Gln Leu Pro Ala Leu Leu Tyr Ala Gln Arg Ser Pro Cys Leu Thr
530                 535                 540 ctc gtg gtc tcg cct ctc ctg tca ctc atg gat gac cag gtg tcc gat     1680
Leu Val Val Ser Pro Leu Leu Ser Leu Met Asp Asp Gln Val Ser Asp
545                 550                 555                 560 ctg cct tca tgt ctg aag gca gcc tgc ctc cac tca gga atg acc aag     1728
Leu Pro Ser Cys Leu Lys Ala Ala Cys Leu His Ser Gly Met Thr Lys
```

-continued

```
                    565                 570                 575
aaa caa cga gag tct gtc ttg aag aag gta cgg gca gcc cag gtg cac    1776
Lys Gln Arg Glu Ser Val Leu Lys Lys Val Arg Ala Ala Gln Val His
            580                 585                 590 gtg ctg atc gtg tcc cca gag gcc ttg gtg ggg tgc ggg gct agg ggt    1824
Val Leu Ile Val Ser Pro Glu Ala Leu Val Gly Cys Gly Ala Arg Gly
        595                 600                 605 ccc ggc agc ctc ccc cag gcc gct cag ctg cct cca att gcc ttc gcc    1872
Pro Gly Ser Leu Pro Gln Ala Ala Gln Leu Pro Pro Ile Ala Phe Ala
    610                 615                 620 tgc att gat gag gtc cac tgc ctc tct cag tgg tca cat aac ttc cgg    1920
Cys Ile Asp Glu Val His Cys Leu Ser Gln Trp Ser His Asn Phe Arg
625                 630                 635                 640 ccc tgc tac cta cgt gtt tgc aaa gtt ctc cgg gag cat atg ggg gtg    1968
Pro Cys Tyr Leu Arg Val Cys Lys Val Leu Arg Glu His Met Gly Val
                645                 650                 655 cgc tgc ttc ttg ggt ctc aca gcc aca gcc aca cga agc act gct cga    2016
Arg Cys Phe Leu Gly Leu Thr Ala Thr Ala Thr Arg Ser Thr Ala Arg
            660                 665                 670 gat gtg gct cag cac ctt ggc ata gct ggc gag ttt gag ctc agc ggg    2064
Asp Val Ala Gln His Leu Gly Ile Ala Gly Glu Phe Glu Leu Ser Gly
        675                 680                 685 tca gcc aac atc cct gcc aat ctg cac ctc tcc gtg tcc atg gat aga    2112
Ser Ala Asn Ile Pro Ala Asn Leu His Leu Ser Val Ser Met Asp Arg
    690                 695                 700 gac tca gac cag gct ctg gtg aca ttg ctg caa ggg gac cgt ttt cgt    2160
Asp Ser Asp Gln Ala Leu Val Thr Leu Leu Gln Gly Asp Arg Phe Arg
705                 710                 715                 720 acc ctg gat tca gtt atc att tac tgc act cgc gaa agg ata cag aac    2208
Thr Leu Asp Ser Val Ile Ile Tyr Cys Thr Arg Glu Arg Ile Gln Asn
                725                 730                 735 ggg tgg ctt gca ctc ctc cgc acc tgc ctg tcc atg gtg ggc gac tca    2256
Gly Trp Leu Ala Leu Leu Arg Thr Cys Leu Ser Met Val Gly Asp Ser
            740                 745                 750 agg cca aga ggc tgt ggc ccc gag gct ata gct gaa gcc tac cat gct    2304
Arg Pro Arg Gly Cys Gly Pro Glu Ala Ile Ala Glu Ala Tyr His Ala
        755                 760                 765 ggc atg agc agc cag gaa cgg cga cga gta caa cag gcc ttc atg cgg    2352
Gly Met Ser Ser Gln Glu Arg Arg Arg Val Gln Gln Ala Phe Met Arg
    770                 775                 780 ggc cac ctg cgc atg gta gtg gcc acg gta gca ttt ggg atg gga ctg    2400
Gly His Leu Arg Met Val Val Ala Thr Val Ala Phe Gly Met Gly Leu
785                 790                 795                 800 gac cgt cca gat gtt cgg gct gtg ctg cac ctg gga ctg cct cca agc    2448
Asp Arg Pro Asp Val Arg Ala Val Leu His Leu Gly Leu Pro Pro Ser
                805                 810                 815 ttc gag agc tac gtg caa gct atc ggc cgt gca ggg cgt gat ggg aag    2496
Phe Glu Ser Tyr Val Gln Ala Ile Gly Arg Ala Gly Arg Asp Gly Lys
            820                 825                 830 cct gcc cat tgc cac cta ttc atg cac ccc cag ggt gaa gac ctt tgg    2544
Pro Ala His Cys His Leu Phe Met His Pro Gln Gly Glu Asp Leu Trp
        835                 840                 845 gaa ctg cgc aga cat gcc cac gct gac agc act gac ttc cta gct gtg    2592
Glu Leu Arg Arg His Ala His Ala Asp Ser Thr Asp Phe Leu Ala Val
    850                 855                 860 aag agg ctg gtg cag cgt gtg ttc cca ccc tgc acc tgc agc cag aga    2640
Lys Arg Leu Val Gln Arg Val Phe Pro Pro Cys Thr Cys Ser Gln Arg
865                 870                 875                 880 cct gtt tcc aag tcc tca cct gag gaa gtc aaa gag cac agt ggc caa    2688
```

```
                Pro Val Ser Lys Ser Ser Pro Glu Glu Val Lys Glu His Ser Gly Gln
                            885                 890                 895 caa aca tac cct gta ctg ggc cag gcc tgc ctg ggc cat gag cgg gca         2736
Gln Thr Tyr Pro Val Leu Gly Gln Ala Cys Leu Gly His Glu Arg Ala
            900                 905                 910 ctc cca gtg cag tct aca gta cag gct ctg gac atg aca gag gag gct         2784
Leu Pro Val Gln Ser Thr Val Gln Ala Leu Asp Met Thr Glu Glu Ala
            915                 920                 925 att gag act ctg ctg tgc tat ttg gaa cta cac cct cgg cac tgg ttg         2832
Ile Glu Thr Leu Leu Cys Tyr Leu Glu Leu His Pro Arg His Trp Leu
            930                 935                 940 gag ctg ctg ccc tgg acc tac gcc cag tgc cat ctg cat tgc ctt ggc         2880
Glu Leu Leu Pro Trp Thr Tyr Ala Gln Cys His Leu His Cys Leu Gly
945                 950                 955                 960 ggc agt gcc cag ctg caa gct ctg gcc cac agg tgt ccc cct ttg gct         2928
Gly Ser Ala Gln Leu Gln Ala Leu Ala His Arg Cys Pro Pro Leu Ala
                965                 970                 975 gca tgc cag gcc aag tgg cca cct aaa gac aca agt cag ggc agg agc         2976
Ala Cys Gln Ala Lys Trp Pro Pro Lys Asp Thr Ser Gln Gly Arg Ser
            980                 985                 990 tcc tta gag ttt ggt gtg gtg gaa  ctg gca gac tcg atg  ggc tgg aag        3024
Ser Leu Glu Phe Gly Val Val Glu  Leu Ala Asp Ser Met  Gly Trp Lys
            995                  1000                 1005 ttg gcc tct gta cgg cag gct ctc cac cag ctg aag tgg gac cca              3069
Leu Ala Ser Val Arg Gln Ala Leu His Gln Leu Lys Trp Asp Pro
    1010                1015                1020 gag cca aag aaa ggc gca gca cag ggc acc gga gtg ctt gtg aag              3114
Glu Pro Lys Lys Gly Ala Ala Gln Gly Thr Gly Val Leu Val Lys
    1025                1030                1035 ttc agc gag ttg gcc ttt cac ctg cac agt cgc ggg gac ctg aca              3159
Phe Ser Glu Leu Ala Phe His Leu His Ser Arg Gly Asp Leu Thr
    1040                1045                1050 gat gag gaa aag gac cag atc tgt gac ttt ctg tac aac cgt gtg              3204
Asp Glu Glu Lys Asp Gln Ile Cys Asp Phe Leu Tyr Asn Arg Val
    1055                1060                1065 cag gct cgt gaa cac aag gcc ctg gcc cac cta cac caa atg tcc              3249
Gln Ala Arg Glu His Lys Ala Leu Ala His Leu His Gln Met Ser
    1070                1075                1080 aag gcc ttt cga agt gtg gcc ttt ccc agt tgt gga ccc tgt tta              3294
Lys Ala Phe Arg Ser Val Ala Phe Pro Ser Cys Gly Pro Cys Leu
    1085                1090                1095 gag cag tct aat gag gag cac agc aat cag gtg aag acc ctg gtc              3339
Glu Gln Ser Asn Glu Glu His Ser Asn Gln Val Lys Thr Leu Val
    1100                1105                1110 agc tac tac ttt gag gaa gag gag gag gag gaa act atg acg              3384
Ser Tyr Tyr Phe Glu Glu Glu Glu Glu Glu Glu Thr Met Thr
    1115                1120                1125 gac act cag ggt cca aaa cct ggg cag act cag ctt cag gac tgg              3429
Asp Thr Gln Gly Pro Lys Pro Gly Gln Thr Gln Leu Gln Asp Trp
    1130                1135                1140 gag gac caa ata cgc cgg gat gtc cgc cag ctc ctg tcc ctg agg              3474
Glu Asp Gln Ile Arg Arg Asp Val Arg Gln Leu Leu Ser Leu Arg
    1145                1150                1155 cca gaa gaa agg ttt tca gga agg gct gtg gcc cgc atc ttc cat              3519
Pro Glu Glu Arg Phe Ser Gly Arg Ala Val Ala Arg Ile Phe His
    1160                1165                1170 ggc att gcg agt cca tgc tac cca gcc cag gtg tat ggg ctg gac              3564
Gly Ile Ala Ser Pro Cys Tyr Pro Ala Gln Val Tyr Gly Leu Asp
    1175                1180                1185
```

```
cgg cgc ttc tgg agg aag tac cta cac ctg gac ttt cat gcc ctg      3609
Arg Arg Phe Trp Arg Lys Tyr Leu His Leu Asp Phe His Ala Leu
    1190                1195                1200 atg cac cta gct aca gaa gag ctc ctg ctg aga ggc cga tga          3651
Met His Leu Ala Thr Glu Glu Leu Leu Leu Arg Gly Arg
    1205                1210                1215
```

<210> SEQ ID NO 2
<211> LENGTH: 1216
<212> TYPE: PRT
<213> ORGANISM: Mus musculus

<400> SEQUENCE: 2

```
Met Glu Arg Leu Ala Thr Val Arg Ala Arg Leu Gln Glu Trp Glu Arg
1               5                   10                  15

Ala Phe Ala Arg Leu His Gly Arg Pro Ala Lys Gly Asp Val Glu
                20                  25                  30

Ala Ala Pro Glu Glu Thr Arg Ala Leu Tyr Arg Glu Tyr Arg Asn Leu
            35                  40                  45

Lys Gln Ala Val Arg Gln Ala Asp Asp Arg His Arg Val Leu Glu Gln
50                  55                  60

Ser Leu Ala Glu Ala Glu Ala Gln Glu Pro Ser Cys Trp Gly
65                  70                  75                  80

Pro His Leu Ser Arg Ala Ala Thr Gln Asn Thr Gln Ser Met Pro Lys
                85                  90                  95

Gln Ser Leu Leu Ser Ser Val Gln Asp Tyr Gly Lys Arg Leu Lys Ala
            100                 105                 110

Asn Leu Lys Asn Thr Thr Gln Thr Gly Pro Thr Gln Ser Arg Lys Leu
        115                 120                 125

Gln Leu Gln Lys Arg Ser Leu Ser Thr Val Pro Ala Pro Arg Pro Pro
130                 135                 140

Gly Ser Lys Thr Glu Ser Pro Cys Pro Asp Glu Ala Asp Asp Ala Leu
145                 150                 155                 160

Pro Arg Val Pro Glu Pro Arg Pro Arg Leu Gly Gln Leu Gln Leu
                165                 170                 175

Arg Ser Ser Leu Ser Arg Arg Leu Thr Ser Leu Asp Pro Gly Trp Leu
            180                 185                 190

Glu Arg Cys His Asn Arg Val Ser Asp Leu Leu Glu Val Pro Gly Ala
        195                 200                 205

Cys Gly Leu Asp Leu Ser Ala Glu Glu Ser Gln Pro Gln Met Ser Gly
210                 215                 220

Lys Val Asn Ile Ala Asp Pro Asp Ile Gln Ser Glu Val Ser Val Gln
225                 230                 235                 240

Ser Pro Glu Ala Ile Ala Gln Gln Pro Ala Gln Val Leu Ser Gln Ser
                245                 250                 255

Pro Lys Ser Ile Asn Ser Lys Gly Arg Lys Arg Lys Trp Asn Glu Lys
            260                 265                 270

Gly Glu Asp Phe Ala Gln Asp Gln Ser Ser Gly Ala Gly Pro Leu
        275                 280                 285

Ser Glu Gly Ala Arg Ala Thr Val His Gly Gln Asp Pro Pro Gly Glu
290                 295                 300

Pro Thr Gln Val Asn Val Pro Gln Pro Cys Asn Ser Ser Asn Gln Ala
305                 310                 315                 320

Arg Thr Glu Lys Ala Lys Gly Thr Thr His Leu His Ala Ser Pro Arg
                325                 330                 335
```

-continued

```
Pro Ala Ser Leu Asp Arg Gly Asn Tyr Ile Arg Leu Asn Met Lys Asn
            340                 345                 350

Lys Arg Phe Val Arg Val Gly Ala Asn Arg Gly Arg Leu Leu Arg Lys
        355                 360                 365

Gln Val Trp Lys Gln Lys Trp Lys Lys Gln Ala Ala Phe Gly Gly
    370                 375                 380

Ser Gly Pro Arg Ala Thr Asp Lys Asp Thr Cys Phe Arg Cys Gly Gln
385                 390                 395                 400

Phe Gly His Trp Ala Ser Gln Cys Ser Gln Pro Gly Pro Thr Leu Thr
                405                 410                 415

Val Gln Glu Glu Gly Asp Arg Asp Lys Gln Pro Ile Ser Thr Leu
            420                 425                 430

Glu Glu Val Ala Gln Arg Thr Gly Thr Ala Ser Cys His His Ser Gly
        435                 440                 445

Glu Glu Thr Gln Pro Ala Ala Pro Glu Leu Gln Val Pro His Cys Pro
    450                 455                 460

Thr Pro Met Ser Pro Leu Tyr Pro Pro Gly Pro Leu Gly Gln Val Ala
465                 470                 475                 480

Glu Thr Pro Ala Glu Val Phe Gln Ala Leu Glu Arg Leu Gly Tyr Arg
                485                 490                 495

Ala Phe Arg Pro Gly Gln Glu Arg Ala Ile Met Arg Ile Leu Ser Gly
            500                 505                 510

Ile Ser Thr Leu Leu Val Leu Pro Thr Gly Ala Gly Lys Ser Leu Cys
        515                 520                 525

Tyr Gln Leu Pro Ala Leu Leu Tyr Ala Gln Arg Ser Pro Cys Leu Thr
    530                 535                 540

Leu Val Val Ser Pro Leu Leu Ser Leu Met Asp Asp Gln Val Ser Asp
545                 550                 555                 560

Leu Pro Ser Cys Leu Lys Ala Ala Cys Leu His Ser Gly Met Thr Lys
                565                 570                 575

Lys Gln Arg Glu Ser Val Leu Lys Lys Val Arg Ala Ala Gln Val His
            580                 585                 590

Val Leu Ile Val Ser Pro Glu Ala Leu Val Gly Cys Gly Ala Arg Gly
        595                 600                 605

Pro Gly Ser Leu Pro Gln Ala Ala Gln Leu Pro Pro Ile Ala Phe Ala
    610                 615                 620

Cys Ile Asp Glu Val His Cys Leu Ser Gln Trp Ser His Asn Phe Arg
625                 630                 635                 640

Pro Cys Tyr Leu Arg Val Cys Lys Val Leu Arg Glu His Met Gly Val
                645                 650                 655

Arg Cys Phe Leu Gly Leu Thr Ala Thr Ala Thr Arg Ser Thr Ala Arg
            660                 665                 670

Asp Val Ala Gln His Leu Gly Ile Ala Gly Glu Phe Glu Leu Ser Gly
        675                 680                 685

Ser Ala Asn Ile Pro Ala Asn Leu His Leu Ser Val Ser Met Asp Arg
    690                 695                 700

Asp Ser Asp Gln Ala Leu Val Thr Leu Leu Gln Gly Asp Arg Phe Arg
705                 710                 715                 720

Thr Leu Asp Ser Val Ile Ile Tyr Cys Thr Arg Glu Arg Ile Gln Asn
                725                 730                 735

Gly Trp Leu Ala Leu Leu Arg Thr Cys Leu Ser Met Val Gly Asp Ser
            740                 745                 750

Arg Pro Arg Gly Cys Gly Pro Glu Ala Ile Ala Glu Ala Tyr His Ala
```

-continued

```
            755                 760                 765
Gly Met Ser Ser Gln Glu Arg Arg Val Gln Gln Ala Phe Met Arg
        770                 775                 780
Gly His Leu Arg Met Val Val Ala Thr Val Ala Phe Gly Met Gly Leu
785                 790                 795                 800
Asp Arg Pro Asp Val Arg Ala Val Leu His Leu Gly Leu Pro Pro Ser
                805                 810                 815
Phe Glu Ser Tyr Val Gln Ala Ile Gly Arg Ala Gly Arg Asp Gly Lys
                820                 825                 830
Pro Ala His Cys His Leu Phe Met His Pro Gln Gly Glu Asp Leu Trp
                835                 840                 845
Glu Leu Arg Arg His Ala His Ala Asp Ser Thr Asp Phe Leu Ala Val
                850                 855                 860
Lys Arg Leu Val Gln Arg Val Phe Pro Pro Cys Thr Cys Ser Gln Arg
865                 870                 875                 880
Pro Val Ser Lys Ser Ser Pro Glu Glu Val Lys Glu His Ser Gly Gln
                885                 890                 895
Gln Thr Tyr Pro Val Leu Gly Gln Ala Cys Leu Gly His Glu Arg Ala
                900                 905                 910
Leu Pro Val Gln Ser Thr Val Gln Ala Leu Asp Met Thr Glu Glu Ala
                915                 920                 925
Ile Glu Thr Leu Leu Cys Tyr Leu Glu Leu His Pro Arg His Trp Leu
                930                 935                 940
Glu Leu Leu Pro Trp Thr Tyr Ala Gln Cys His Leu His Cys Leu Gly
945                 950                 955                 960
Gly Ser Ala Gln Leu Gln Ala Leu Ala His Arg Cys Pro Pro Leu Ala
                965                 970                 975
Ala Cys Gln Ala Lys Trp Pro Pro Lys Asp Thr Ser Gln Gly Arg Ser
                980                 985                 990
Ser Leu Glu Phe Gly Val Val Glu Leu Ala Asp Ser Met Gly Trp Lys
                995                1000                1005
Leu Ala Ser Val Arg Gln Ala Leu His Gln Leu Lys Trp Asp Pro
        1010                1015                1020
Glu Pro Lys Lys Gly Ala Ala Gln Gly Thr Gly Val Leu Val Lys
        1025                1030                1035
Phe Ser Glu Leu Ala Phe His Leu His Ser Arg Gly Asp Leu Thr
        1040                1045                1050
Asp Glu Glu Lys Asp Gln Ile Cys Asp Phe Leu Tyr Asn Arg Val
        1055                1060                1065
Gln Ala Arg Glu His Lys Ala Leu Ala His Leu His Gln Met Ser
        1070                1075                1080
Lys Ala Phe Arg Ser Val Ala Phe Pro Ser Cys Gly Pro Cys Leu
        1085                1090                1095
Glu Gln Ser Asn Glu Glu His Ser Asn Gln Val Lys Thr Leu Val
        1100                1105                1110
Ser Tyr Tyr Phe Glu Glu Glu Glu Glu Glu Glu Thr Met Thr
        1115                1120                1125
Asp Thr Gln Gly Pro Lys Pro Gly Gln Thr Gln Leu Gln Asp Trp
        1130                1135                1140
Glu Asp Gln Ile Arg Arg Asp Val Arg Gln Leu Leu Ser Leu Arg
        1145                1150                1155
Pro Glu Glu Arg Phe Ser Gly Arg Ala Val Ala Arg Ile Phe His
        1160                1165                1170
```

Gly Ile Ala Ser Pro Cys Tyr Pro Ala Gln Val Tyr Gly Leu Asp
    1175                1180                1185

Arg Arg Phe Trp Arg Lys Tyr Leu His Leu Asp Phe His Ala Leu
    1190                1195                1200

Met His Leu Ala Thr Glu Glu Leu Leu Leu Arg Gly Arg
    1205                1210                1215

<210> SEQ ID NO 3
<211> LENGTH: 180
<212> TYPE: DNA
<213> ORGANISM: Mus musculus

<400> SEQUENCE: 3
gttctccggg agcatatggg ggtgcgctgc ttcttgggtc tcacagccac agccacacga    60
agcactgctc gagatgtggc tcagcacctt ggcatagctg gcgagtttga gctcagcggg   120
tcagccaaca tccctgccaa tctgcacctc tccgtgtcca tggatagaga ctcagaccag   180

<210> SEQ ID NO 4
<211> LENGTH: 30
<212> TYPE: DNA
<213> ORGANISM: Artificial
<220> FEATURE:
<223> OTHER INFORMATION: PCR primer

<400> SEQUENCE: 4
cttttgcacg gctgcacggg cgacggccag                                     30

<210> SEQ ID NO 5
<211> LENGTH: 30
<212> TYPE: DNA
<213> ORGANISM: Artificial
<220> FEATURE:
<223> OTHER INFORMATION: PCR primer

<400> SEQUENCE: 5
cagctatgcc aaggtgctga gccacatctc                                     30

<210> SEQ ID NO 6
<211> LENGTH: 30
<212> TYPE: DNA
<213> ORGANISM: Artificial
<220> FEATURE:
<223> OTHER INFORMATION: PCR primer

<400> SEQUENCE: 6
ttgagctcag cgggtcagcc aacatccctg                                     30

<210> SEQ ID NO 7
<211> LENGTH: 30
<212> TYPE: DNA
<213> ORGANISM: Artificial
<220> FEATURE:
<223> OTHER INFORMATION: PCR primer

<400> SEQUENCE: 7
tgctctaaac agggtccaca actgggaaag                                     30

<210> SEQ ID NO 8
<211> LENGTH: 583
<212> TYPE: DNA
<213> ORGANISM: Artificial
<220> FEATURE:
<223> OTHER INFORMATION: PCR primer

<400> SEQUENCE: 8

```
ggacactcag ggtccaaaac ctgggcagac tcaggtaagt gccacacctc tgaggatagt    60
tcttaaagct tgggacagtg acatggcccc attcaaccct gacccacag ttcaatccct    120
gcttggctca aggtttcctt ggctgctccg ggtgtgattt tacatgacag atgctatggt    180
agctcagatg aggttacatg ctatcctccc acagcttcag gactgggagg accaaatacg    240
ccgggatgtc cgccagctcc tgtccctgag gccagaagaa aggttttcag gaagggctgt    300
ggcccgcatc ttccatggca ttggtgaggg ccacggggtt gcctggtgcc agcgggggat    360
gggtattaga gccagctgag tcctcaggcc tgtgtttctg ctccacccta gcgagtccat    420
gctacccagc ccaggtgtat gggctggacc ggcgcttctg gaggaagtac ctacacctgg    480
actttcatgc cctgatgcac ctagctacag aagagctcct gctgagaggc cgatgaccac    540
cttacatggg agggtgccac atgattgagg catgaggcaa gcc                      583
```

<210> SEQ ID NO 9
<211> LENGTH: 30
<212> TYPE: DNA
<213> ORGANISM: Artificial
<220> FEATURE:
<223> OTHER INFORMATION: PCR primer

<400> SEQUENCE: 9

```
ctcgtggtct cgcctctcct gtcactcatg                                      30
```

<210> SEQ ID NO 10
<211> LENGTH: 30
<212> TYPE: DNA
<213> ORGANISM: Artificial
<220> FEATURE:
<223> OTHER INFORMATION: PCR primer

<400> SEQUENCE: 10

```
gcccaccatg gacaggcagg tgcggaggag                                      30
```

<210> SEQ ID NO 11
<211> LENGTH: 30
<212> TYPE: DNA
<213> ORGANISM: Artificial
<220> FEATURE:
<223> OTHER INFORMATION: PCR primer

<400> SEQUENCE: 11

```
cttgggaaaa gcgcctcccc tacccggtag                                      30
```

<210> SEQ ID NO 12
<211> LENGTH: 30
<212> TYPE: DNA
<213> ORGANISM: Artificial
<220> FEATURE:
<223> OTHER INFORMATION: PCR primer

<400> SEQUENCE: 12

```
ctcgtggtct cgcctctcct gtcactcatg                                      30
```

<210> SEQ ID NO 13
<211> LENGTH: 30
<212> TYPE: DNA
<213> ORGANISM: Artificial
<220> FEATURE:
<223> OTHER INFORMATION: PCR primer

```
-continued

<400> SEQUENCE: 13
cagctgggca ctgccgccaa ggcaatgcag                               30

<210> SEQ ID NO 14
<211> LENGTH: 20
<212> TYPE: DNA
<213> ORGANISM: Artificial
<220> FEATURE:
<223> OTHER INFORMATION: PCR primer

<400> SEQUENCE: 14
ctgcctctct cagtggtcac                                          20

<210> SEQ ID NO 15
<211> LENGTH: 20
<212> TYPE: DNA
<213> ORGANISM: Artificial
<220> FEATURE:
<223> OTHER INFORMATION: PCR primer

<400> SEQUENCE: 15
gacaggcagg tgcggaggag                                          20

<210> SEQ ID NO 16
<211> LENGTH: 30
<212> TYPE: DNA
<213> ORGANISM: Artificial
<220> FEATURE:
<223> OTHER INFORMATION: PCR primer

<400> SEQUENCE: 16
ctcgtggtct cgcctctcct gtcactcatg                               30

<210> SEQ ID NO 17
<211> LENGTH: 30
<212> TYPE: DNA
<213> ORGANISM: Artificial
<220> FEATURE:
<223> OTHER INFORMATION: PCR primer

<400> SEQUENCE: 17
cagctgggca ctgccgccaa ggcaatgcag                               30
```

MOUSE EXHIBITING CHARACTERISTICS OF ROTHMUND-THOMSON SYNDROME AND PREPARATION METHOD THEREOF

This is a continuation application of PCT/JP2004/009380 with an International Filing Date of Jun. 25, 2004.

TECHNICAL FIELD

The present invention relates to a non-human mammal, especially a mouse exhibiting a characteristic of Rothmund-Thomson syndrome and a preparation method thereof. Specifically, the present invention relates to a mouse which has a mutation in exon 13 of RECQL4 gene and exhibits a characteristic of Rothmund-Thomson syndrome and a preparation method thereof.

BACKGROUND ART

Rothmund reported a disease characterized by poikiloderma and juvenile cataract (Rothmund, A. (1868) Uber cataracten in verbindung mit einer eigenthumlichen hautdegeneration. Arch. Klin. Exp. Ophthal., 4, 159-182.). Thomson reported a disease characterized by poikiloderma and genetic osteogenesis abnormalities (Thomson, M. S. (1936) Poikiloderma congenitale. Br. J. Dermatol., 48, 221-234). These diseases were later found to be part of the same syndrome, designated Rothmund-Thomson syndrome. Rothmund-Thomson syndrome (hereinafter abbreviated "RTS") is an autosomal recessive genetic disease characterized by growth disorder, poikiloderma, hair loss, cataracts, osteogenesis abnormalities and a high incidence of osteosarcomas (Ichikawa, K., Noda, T. and Furuichi, Y. (2002) Preparation of the gene targeted knockout mice for human premature aging diseases, Werner syndrome, and Rothmund-Thomson syndrome caused by the mutation of DNA helicases. Nippon Yakurigaku Zasshi., 119, 219-226., Vennos, E. M. and James, W. D. (1995) Rothmund-Thomson syndrome. Dermatol. Clin., 13, 143-150., Vennos, E. M., Collins, M. and James, W. D. (1992) Rothmund-Thomson syndrome: review of the world literature. J. Am. Acad. Dermatol., 27, 750-762).

These characteristics also suggest that RTS is a premature aging syndrome. Werner's syndrome which is caused by mutation in WRN gene and Bloom syndrome which is caused by mutation in BLM gene, have been known as typical examples of premature aging syndrome (Mohaghegh, P. and Hickson, I. D. (2001) DNA helicase deficiencies associated with cancer predisposition and premature ageing disorders. Hum. Mol. Genet., 10, 741-746).

The genes belong to RecQ helicase gene family. For RECQL4 gene which belongs to the RecQ helicase gene family, mutations of the RECQL4 gene is identified in many RTS patients. The mutations were frequently identified in the helicase domain of RECQL4 gene (FIG. 1. Arrows). In order to confirm whether RTS is caused by the mutations in the helicase domain of RECQL4 gene to prepare a mouse model for RTS patient, preparation of a RECQL4 gene-disrupted mouse was attempted. However, the mouse wherein exons 5 to 8 in the twenty two exons of RECQL4 gene are knockouted was died between embryonic day 3.5 to 6.5 (Ichikawa, K., Noda, T. and Furuichi, Y. (2002) Preparation of the gene targeted knockout mice for human premature aging diseases, Werner syndrome, and Rothmund-Thomson syndrome caused by the mutation of DNA helicases. Nippon Yakurigaku Zasshi., 119, 219-226). Therefore, the preparation of the mouse model for RTS had not been unsuccessful.

DISCLOSURE OF THE INVENTION

An object of the present invention is to provide a non-human mammal, especially a mouse exhibiting a characteristic of Rothmund-Thomson syndrome and a preparation method thereof. Specifically, the present invention relates to a mouse which has a mutation in exon 13 of RECQL4 gene and exhibits a characteristic of Rothmund-Thomson syndrome and a preparation method thereof.

The present inventor found that a RECQL4 gene-deficient mouse could be prepared by modifying only the exon 13 of the mouse RECQL4 gene (hereinafter, "RECQL4 gene" may be simply referred to as "Recql4") and the obtained mouse exhibited at least some characteristics of Rothmund-Thomson syndrome. The present invention was achieved based on these finding.

Accordingly, the present invention relates to:

(1) A non-human mammal exhibiting a characteristic of Rothmund-Thomson syndrome;

(2) A rodent animal exhibiting a characteristic of Rothmund-Thomson syndrome;

(3) A mouse exhibiting a characteristic of Rothmund-Thomson syndrome;

(4) The mouse according to (3), wherein exon 13 of RECQL4 gene is mutated and exons 14 to 22 of RECQL4 gene encode amino acid sequences corresponding to those encoded by exons 14 to 22 of the wild-type RECQL4 gene;

(5) A RECQL4 gene-deficient mouse, wherein exon 13 of RECQL4 gene is mutated and exons 14 to 22 of RECQL4 gene encode amino acid sequences corresponding to those encoded by exons 14 to 22 of the wild-type RECQL4 gene;

(6) The mouse according to (4) or (5), wherein exon 13 of RECQL4 gene has the sequence shown in SEQ ID NO: 3;

(7) The mouse according to any one of (3) to (6), wherein RECQL4 loses a helicase activity;

(8) A method for preparing the mouse according to any one of (3) to (7) comprising the step of introducing a mutation into exon 13 of RECQL4 gene;

(9) The method according to (8), wherein the whole exon 13 of RECQL4 gene in the resultant mouse is deleted;

(10) The method according to (8) or (9), wherein exons 14 to 22 of RECQL4 gene in the resultant mouse encode amino acid sequences corresponding to those encoded by exons 14 to 22 of the wild-type RECQL4 gene;

(11) The method according to any one of (8) to (10), wherein exon 13 of RECQL4 gene has the sequence shown in SEQ ID NO.: 3; and

(12) The method according to any one of (8) to (11), wherein the introduction of the mutation into exon 13 of RECQL4 gene is carried out with gene targeting.

"TK" indicates thymidine kinase gene. "Neo'" indicates neomycin-resistance gene. Arrows indicate the direction of transcription.

"X" indicates the recognition site of the restriction enzyme XbaI.

"3' probe" indicates the region used as probes for Southern hybridization.

Arrowheads indicate primers used for RT-PCR.

Figure 3:
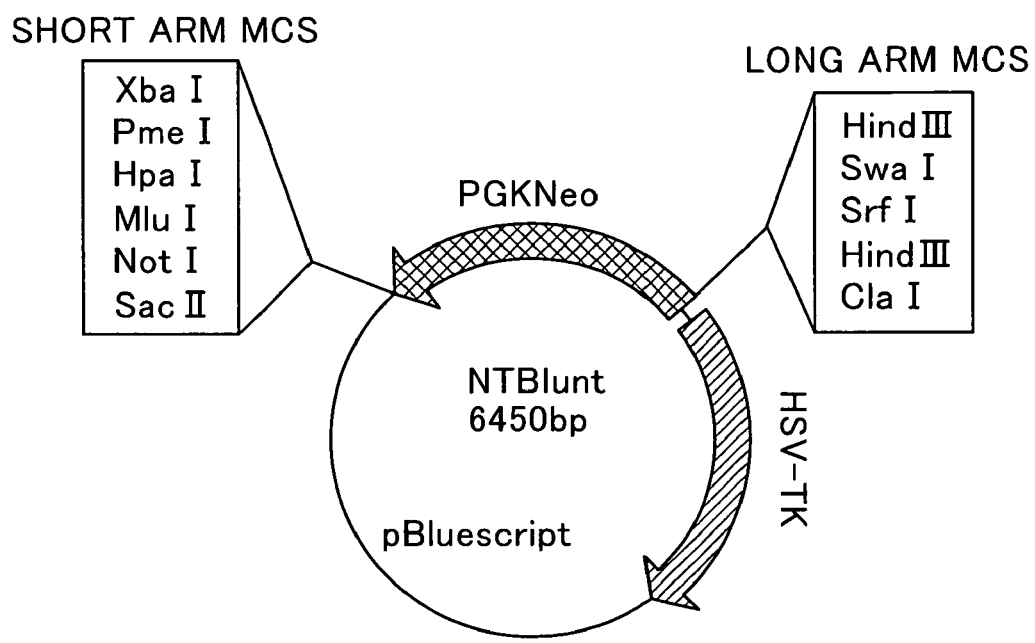

FIG. 3 shows a NTBlunt vector which is the basis of the preparation of a gene targeting vector for disrupting exon 13 of RECQL4 gene.

Figure 4:
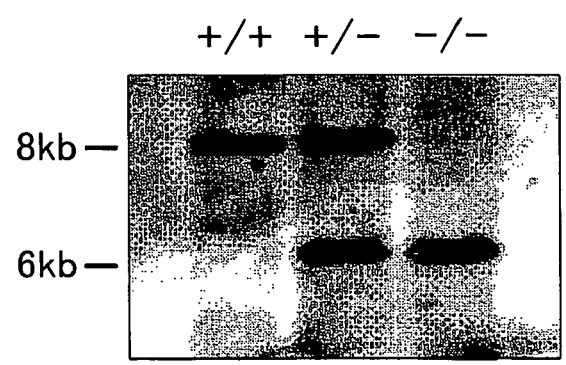

FIG. 4 shows the result of Southern hybridization using 3' probe of Recql4 gene for DNA extracted from a part of tail of the following mice: wild-type mouse (Recql4 +/+), RECQL4 gene-deficient heterozygous mouse (Recql4 +/−) and RECQL4 gene-deficient homozygous mouse (Recql4 −/−).

FIG. 5 shows the cDNA sequences identified from the mouse RECQL4 gene transcripts obtained before and after gene targeting.

FIG. 6 shows the result of quantitative PCR for the exon 13-deleted transcript of RECQL4 gene-deficient homozygous mouse (Recql4 −/−)

Figure 7:
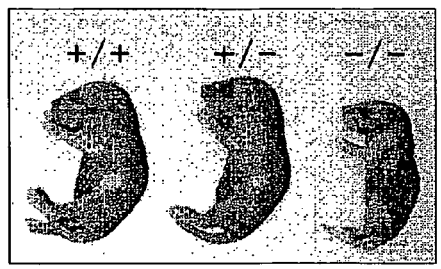

FIG. 7 shows the appearance of the wild-type mouse (Recql4 +/+), RECQL4 gene-deficient heterozygous mouse (Recql4 +/−) and RECQL4 gene-deficient homozygous mouse (Recql4 −/−) at day 19.

Figure 8:
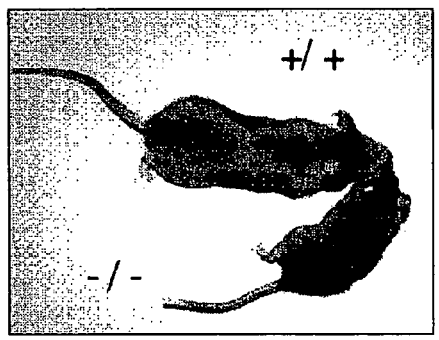

FIG. 8 shows the appearance of the wild-type mouse (Recql4 +/+), RECQL4 gene-deficient heterozygous mouse (Recql4 +/−) and RECQL4 gene-deficient homozygous mouse (Recql4 −/−) at 10 weeks after birth.

Figure 9:
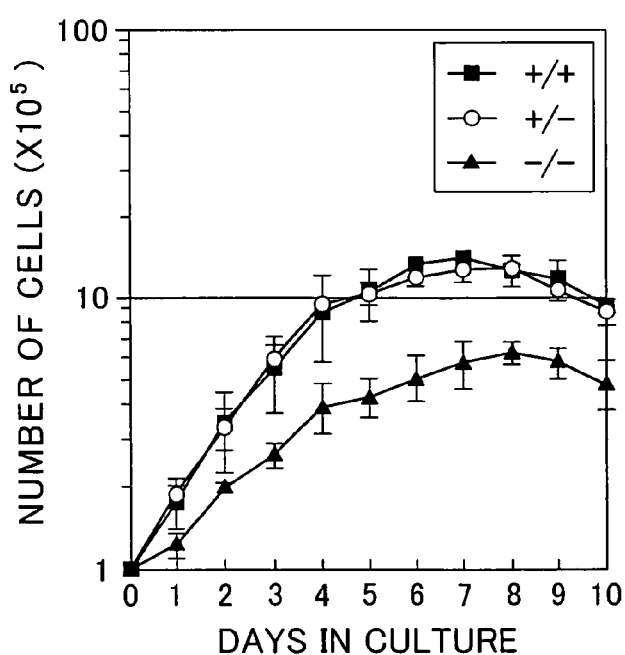

FIG. 9 shows cell growth curves of MEFs derived from the wild-type mouse (Recql4 +/+), RECQL4 gene-deficient heterozygous mouse (Recql4 +/−) and RECQL4 gene-deficient homozygous mouse (Recql4 −/−).

BEST MODE FOR CARRYING OUT THE INVENTION

In the present specification, the phrase "exhibiting a characteristic of Rothmund-Thomson syndrome (RTS)" means that one exhibits at least one of characteristics of human RTS such as skin abnormalities (poikiloderma, colorless hair and hair loss), short stature (short length), osteogenesis abnormalities, cataracts, immunological abnormalities, sterility and malignancies (see Table 1 below).

In the present specification, the term "RECQL4 gene-deficient mouse" means a mouse which has a mutation in RECQL4 gene and wherein RECQL4 protein does not normally function, especially, a mouse wherein the helicase activity of RECQL4 protein is lost. The "RECQL4 gene-deficient mouse" of the present invention exhibits a characteristic of Rothmund-Thomson syndrome.

In the animal of the present invention, mutation is introduced into exon 13 of RECQL4 gene, thereby the function of RECQL4 protein, especially helicase activity of the RECQL4 protein, was lost.

The cDNA sequence of mouse RECQL4 is shown in SEQ ID NO.: 1. The amino acid sequence of mouse RECQL4 is shown in SEQ ID NO.: 2. In one embodiment of the present invention, exon 13 has the sequence shown in SEQ ID NO.: 3. The sequence of exon 13 shown in SEQ ID NO.: 3 corresponds to the nucleotide sequence at the positions 1945 to 2124 of SEQ ID NO.: 1.

In one embodiment of the present invention, whole exon 13 of RECQL4 gene was deleted. Exon 13 (180 bp) encodes an amino acid sequences that play an essential role in helicase activity. Exon 13 has the length of a multiple of 3 (180 bp). Therefore, when whole exon 13 is excluded from the normal splicing, the frame (reading frame of the amino acid sequence) in the subsequent exons 14 to 22 is conserved and therefore the exons encode a protein which is homologous with the wild-type Recql4 protein. Each of exons 14 to 22 is not one whose the number of constitutive base is a multiple of 3. Therefore, among exons 1 to 22, exon 13 presents at the extreme C terminal side of RECQL4 gene as the exon whose length is a multiple of 3. Therefore, in the RECQL4 gene-deficient mouse of the present invention, exons 14 to 22 of RECQL4 gene preferably encode the amino acid sequences which correspond to the amino acid sequences encoded by exons 14 to 22 of the wild-type RECQL4 gene.

RECQL4 protein belongs to the helicase super family II (SFII) that includes seven conserved motifs, of which exon 13 encodes motif III. On the basis of an X-ray structural analysis of the putative RNA helicase, it has been reported that the TAT (SAT) sequence in motif III plays a critical role in helicase activity which requires the hydrolysis of ATP, and its binding to DNA (Story, R. M., Li, H. and Abelson, J. N. (2001) Crystal structure of a DEAD box protein from the hyperthermophile *Methanococcus jannaschii*. Proc. Natl. Acad. Sci. U.S.A., 98, 1465-1470). Furthermore, it has been reported that mutation of the SAT motif in mouse eIF4a (also part of SFII) (Pause, A. and Sonenberg, N. (1992) Mutational analysis of a DEAD box RNA helicase: the mammalian translation initiation factor eIF-4A. EMBO J., 11, 2643-2654.) and mutation of motif III of mouse Blm (Bahr, A., De Graeve, F., Kedinger, C. and Chatton, B. (1998) Point mutations causing Bloom's syndrome abolish ATPase and DNA helicase activities of the BLM protein. Oncogene, 17, 2565-2571.) inhibit its helicase activity. Furthermore, it has been reported that mutation of TAT in the *E. coli* RecG helicase inhibits branch migration. These findings indicate that motif III is essential to the helicase activity. Therefore, in one embodiment of the present invention, mutation for disrupting motif III of exon 13 may be introduced into an animal. In this case, in the RECQL4 gene-deficient mouse of the present invention, exons 14 to 22 of RECQL4 gene preferably encode the amino acid sequences which correspond to the amino acid sequences encoded by exons 14 to 22 of the wild-type RECQL4 gene.

When a non-human mammal other than mouse, especially a rodent animal is subjected to gene targeting, exon containing motif III can be targeted to the gene transfer to introduce a mutation having the above-mentioned characteristics into the mammal.

In the present invention, mouse strain 129/SV which is generally used for the preparation of a mouse model, can be used as a mouse.

In the present invention, the introduction of the mutation into RECQL4 gene can be carried out by so-called gene targeting.

Figure 1:
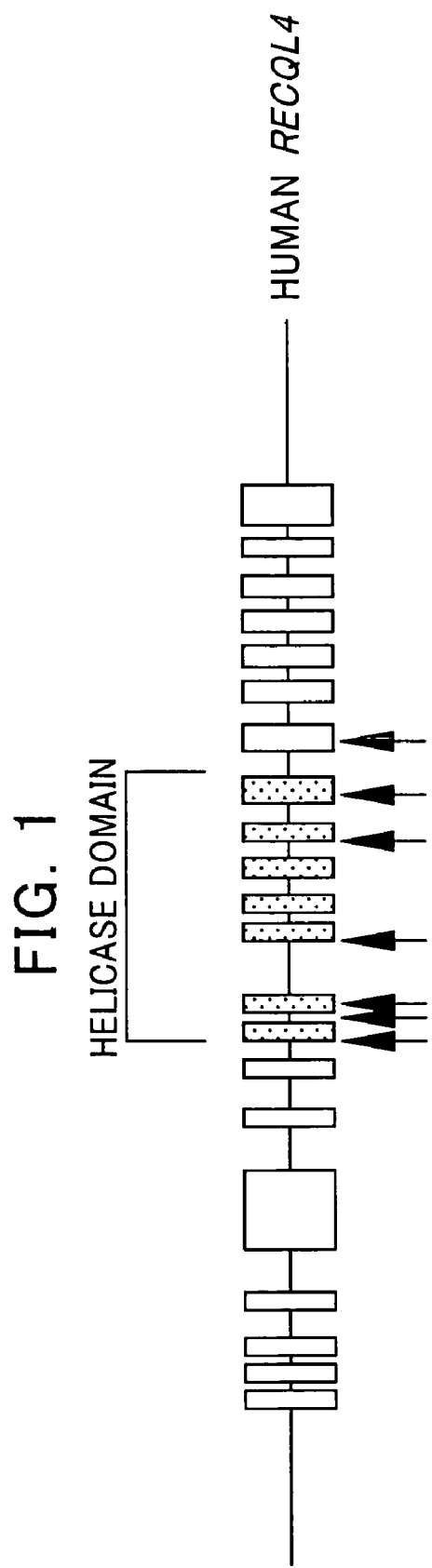
FIG. 1 is a diagram showing positions of mutations as identified in RECQL4 gene of human RTS patient. Arrows indicate mutations. Boxes indicate exons. Shaded boxes indicate exons coding the RecQ-helicase domain.
Figure 2:
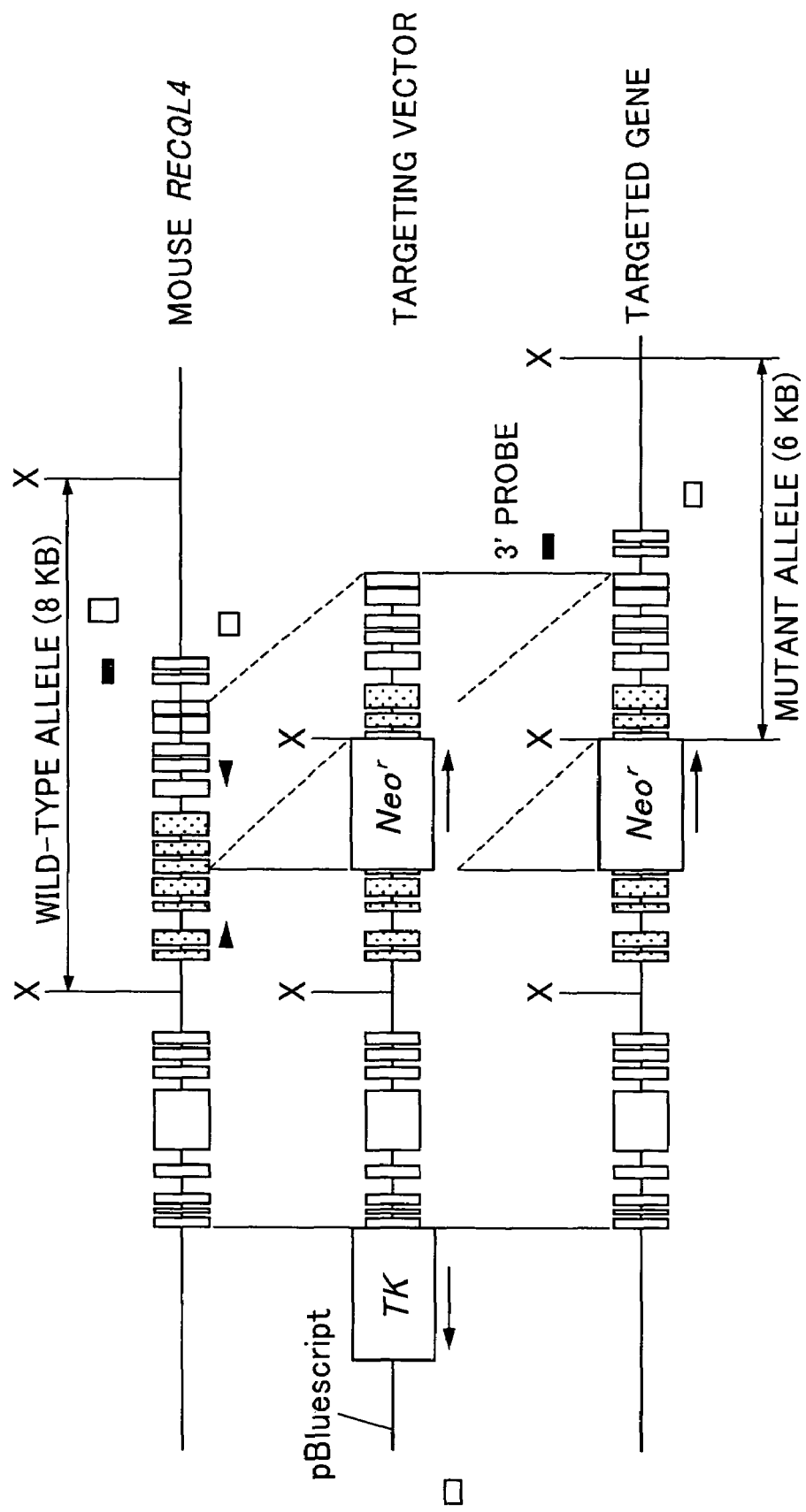
FIG. 2 is a schematic diagram showing a method for preparing a RECQL4 gene-deficient homozygous mouse (Recql4 −/−). Upper diagram indicates the structure of RECQL4 gene of the wild-type mouse. Middle diagram indicates the structure of a gene targeting vector. Lower diagram indicates the structure of RECQL4 gene after homologous recombination by gene targeting technique.

As a targeting vector for preparing a mouse of the present invention, for example, a vector containing:

(1) a positive selective marker;

(2) a sequence (Long arm) which is present at the 5'-end side region relative to the positive selective marker and is homologous to the sequence of exons 1 to 12 of the RECQL4 gene or a part thereof; and (3) a sequence (Short arm) which is present at the 3'-end side region relative to the positive selective marker and is homologous to the sequence of exons 14 to 20 of the RECQL4 gene or a part thereof, can be used (FIG. 2, middle diagram).

It is generally preferable that both Long arm and Short arm have the longer length. For example, it is much preferable that the sequence at the 5'-end side region contains exons 1 to 12 of RECQL4 gene and has a length of 4 kb or more. However, the length of the sequences at 3'- and 5'-end side regions is not critical for the present invention, and is sufficient to be a length which can be generally used for gene targeting. The sequence of a region in the targeting vector where homologous recombination occurs, is not required to completely coincides with that of a target region in a target animal, and is sufficient to have a sequence similarity with that of the target region in the target animal enough to cause the homologous recombination.

As a positive selective marker, a drug resistance gene, for example, neomycin-resistance gene, hygromycin-resistance gene and puromycin-resistance gene can be generally used.

The targeting vector further may contain a negative selective marker to confirm the occurrence of the homologous recombination. As the negative selective marker, thymidine kinase gene and diphtheria toxin A gene can be used.

The targeting vector is introduced into an embryo stem cell (ES cell). The introduction method is not limited to any specific method. Any methods and conditions which are known to be generally employed for gene targeting by a person skilled in the art, can be used. For example, electroporation and lipofectin method etc. can be used.

The obtained targeting vector-introduced ES cell can be cultured under a suitable condition. For example, the targeting vector-introduced ES cell can be cultured in a medium which is suitable for culturing ES cell and contains an agent corresponding to the positive selective marker and an agent corresponding to the negative selective marker. Culture condition and method for ES cell are well known to a person skilled in the art. If necessary, the presence, position and orientation of the introduced gene in the targeting vector-introduced ES cell can be confirmed by PCR.

The obtained RECQL4 gene-deficient heterozygous ES cell (Recql4 +/−) is microinjected into blastocyst in accordance with a method which is well-known to a person skilled in the art. The obtained blastocyst can be introduced into a pseudopregnant animal to prepare a chimeric animal wherein a desired gene is introduced. The obtained chimeric animal can be selected for the presence of the introduced gene based on the characteristics derived from the ES cell, such as hair color.

The selected animal is bred with an animal having no gene introduction to prepare a progeny animal (F1 animal). The obtained progeny animal can be further selected based on the characteristics derived from the ES cell, such as hair color, to obtain an animal wherein the introduced gene is present in germline. If necessary, the presence of the introduced gene in the obtained animal can be confirmed by PCR using a sample from the obtained animal, for example, DNA extracted from a tail of the animal. Thus obtained RECQL4 gene-deficient heterozygous animals (Recql4 +/−) can be intercrossed to produce a RECQL4 gene-deficient homozygous animal (Recql4 −/−), for example, a mutant animal wherein whole exon 13 of RECQL4 gene is deleted.

The characteristics of the obtained RECQL4 gene-deficient animal (Recql4 −/−) can be examined by using the wild-type animal (Recql4 +/+) as a control. For example, observation of appearance of the animal, observation of the state of the skin, measurement of incidence of malignancies, measurement of the amount of Recql4 transcript, observation of tissue specimen, cytological analysis and so on, can be carried out. The amount of transcript can be quantitatively determined by subjecting total RNA or poly(A) RNA to RT-PCR. The observation of tissue specimen can be carried out with a sectioned tissue sample which is prepared by fixing a tissue sample in formalin and embedding the fixed sample in paraffin in accordance with the common procedures. The cytological analysis can be carried out by examining cells which are isolated from the animal tissue for their sensitivity to various stimulations, especially the sensitivity to radiation or ultraviolet rays. Furthermore, growth ability of the animal can be measured based on weight, length and height of the animal after breeding for a certain period.

The RECQL4 gene-deficient animal (Recql4 −/−) of the present invention, especially the RECQL4 gene-deficient mouse exhibits severe hair loss and lesion with erosive bleeding. Furthermore, RECQL4 gene-deficient animals of the present invention exhibits hypoplasia of epidermis, dermis and subcutaneous tissue. The RECQL4 gene-deficient animal of the present invention, especially the RECQL4 gene-deficient mouse exhibits bony dysplasia, especially trabecula dysplasia. Furthermore, the RECQL4 gene-deficient animal of the present invention, especially the RECQL4 gene-deficient mouse exhibits growth retardation. The size of the RECQL4 gene-deficient mouse at 10 weeks after birth is approximately half and one-third that of the wild-type mouse. Furthermore, the growth rate of cells obtained from the RECQL4 gene-deficient mouse decreases to two-third that of the wild-type cells. Furthermore, the RECQL4 gene-deficient animal of the present invention, especially RECQL4 gene-deficient mouse exhibits a decreased size and number of villi in the small intestine as compared to those of the wild-type mouse.

Table 1 shows the comparison of the characteristics of the RECQL4 gene-deficient mouse of the present invention with the symptoms of human RTS. This results indicate that the RECQL4 gene-deficient animal, especially the RECQL4 gene-deficient mouse can be used as an animal model for Rothmund-Thomson syndrome (RTS). In the present specification, the phrase "exhibiting a characteristic of Rothmund-Thomson syndrome (RTS)" means that one exhibits at least one of the characteristics of RTS shown in Table 1 below.

TABLE 1

Comparison of the characteristics of the RECQL4 gene-deficient animal of the present invention with the symptoms of human RTS.

| Characteristics/ Symptoms | RTS | Recql4 gene-deficient mouse |
|---|---|---|
| Skin abnormalities | | |
| Poikiloderma | + | − |
| Colorless hair | + | + |
| Hair loss | + | + |
| Short stature (length) | + | + |
| Osteogenesis abnormalities | + | + |
| Cataracts | + | −[b] |
| Immunological abnormalities | Rare | +[c] |
| Sterility | + | +[d] |
| Malignancies | + | −[b] |
| X-ray high sensitivity | ?[a] | −[e] |
| UV high sensitivity | ?[a] | −[e] |

[a]Some RTS patient's cells are sensitive to X-rays or UV-rays, but others are not.
[b]2 to 8 weeks old mice (n = 23).
[c]Fewer T cells were observed.
[d]Histological studies indicate that the Recql4 gene-deficient mouse exhibits normal spermatogenesis. However, when the Recql4 gene-deficient mouse was bred with C57BL/6 mouse or littermate thereof, no newborn mouse was obtained (male: n = 5; female: n = 4).
[e]MEFs

EXAMPLE 1

Construction of Targeting Vector

A targeting vector was constructed by inserting Long arm and Short arm into NTBlunt vector which contains neomycin-resistance gene as a positive selective marker, thymidine kinase gene as a negative selective marker (Unless homologous recombination were occurred, the thymidine kinase gene were incorporated into a cell and rendered the cell lethal sensitive to ganciclovir).

NTBlunt vector was produced by digesting pKJ1 vector carrying neomycin-resistance gene (PGKNeo) (NAR, vol 19, no. 20 5755-5761, 1991. McBurney M W et. al.) with restriction enzymes EcoRI and BgIII, inserting the obtained PGK-NeopA into pBluescriptII which was digested with restriction enzymes EcoRI and BamHI, and inserting thymidine kinase gene (HSV-TK) into the obtained vector in accordance with common procedures.

Long arm (the 5'-end side region relative to the positive selective marker) was prepared by means of PCR with 4.3 kb genomic DNA containing exons 1 to 12 of Recql4 gene of mouse ES cell (which was prepared from ES cell line R1 with conventional phenol/chloroform extraction) as template and the following primers:

```
                                               (SEQ ID NO.: 4)
mQ4-1(+)30
5'-CTTTTGCACGGCTGCACGGGCGACGGCCAG-3'

(SEQ ID NO.: 5)
mQ4-Co1(-)30
5'-CAGCTATGCCAAGGTGCTGAGCCACATCTC-3'
```

Short arm (the 3'-end side region relative to the positive selective marker) was prepared by means of PCR with 1.9 kb genomic DNA containing exons 14 to 20 of Recql4 gene of mouse ES cell (which was prepared from ES cell line R1 with conventional phenol/chloroform extraction) as template and the following primers:

```
                                               (SEQ ID NO.: 6)
mQ4-6(+)30
5'-TTGAGCTCAGCGGGTCAGCCAACATCCCTG-3'

(SEQ ID NO.: 7)
mQ4-9(-)30
5'-TGCTCTAAACAGGGTCCACAACTGGGAAAG-3'
```

PCR was carried out using KODplus polymerase (TOYOBO) in accordance with the manufacturer's protocols.

Short arm and Long arm were inserted into the recognition sites of the restriction enzymes HpaI and SwaI in NTBlunt vector, respectively in accordance with common procedures. NTBlunt vector which was the basis of the preparation of the targeting vector was shown in FIG. 3.

Gene Targeting of Recql4 Gene

Mouse ES cell to be used for the targeting vector was mouse ES cell line R1 (The cell line R1 was obtained from Dr. Nagy. Contact address: Division of Molecular and Developmental Biology, Samuel Lumenfeld Research Institute, Mount Sinai Hospital, Toronto, ON, Canada) (Nagy, A., Rossant, J., Nagy, R., Abramow-Newerly, W. and Roder, J. C. (1993) Derivation of completely cell culture-derived mice from early-passage embryonic stem cells. Proc. Natl. Acad. Sci. U.S.A., 90, 8424-8428.).

Thirty micro grams of the targeting vector and $2 \times 10^7$ cells of R1 cells were added into a cuvette (electrode gap: 4 mm) (BioRad) and were subjected to electroporation (voltage: 250V; capacity: 950 micro F) using GenePulserII (BioRad) to introduce the targeting vector into the mouse ES cells.

The obtained targeting vector-introduced ES cells were cultured in a medium containing a selective agent G418 (For positive selection. neomycin derivative) and ganciclovir (For negative selection) in accordance with Nagy et al. (Proc Natl Acad Sci USA. 1993 Sep. 15; 90(18):8424-8. Derivation of completely cell culture-derived mice from early-passage embryonic stem cells.; Nagy A, Rossant J, Nagy R, Abramow-Newerly W, Roder J C. Division of Molecular and Developmental Biology, Samuel Lumenfeld Research Institute, Mount Sinai Hospital, Toronto, ON, Canada.).

Cell clones which exhibited resistance against both G418 and ganciclovir were cultured and genomic DNA thereof were extracted in accordance with common procedures. The extracted genomic DNA was digested with restriction enzyme XbaI. The digested genomic DNA was subjected to agarose gel electrophoresis and was transferred to a nylon membrane. Then, Southern hybridization (Wurst, W. and Joyner, A. L. (1993) Gene targeting: A Practical Approach. IRL press, Oxford.) was carried out by using a fluorescence-labeled probe (shown as "3' probe" in FIG. 2) corresponding to the DNA fragment of 0.6 kb genomic region containing exons 21 and 22 of Recql4 gene as follows:

```
                                               (SEQ ID NO.: 8)
5'-GGACACTCAGGGTCCAAAACCTGGGCAGACTCAGGTAAGTGCCACAC

CTCTGAGGATAGTTCTTAAAGCTTGGGACAGTGACATGGCCCCATTCAAC

CCTGACCCCACAGTTCAATCCCTGCTTGGCTCAAGGTTTCCTTGGCTGCT

CCGGGTGTGATTTTACATGACAGATGCTATGGTAGCTCAGATGAGGTTAC

ATGCTATCCTCCCACAGCTTCAGGACTGGGAGGACCAAATACGCCGGGAT

GTCCGCCAGCTCCTGTCCCTGAGGCCAGAAGAAAGGTTTTCAGGAAGGGC

TGTGGCCCGCATCTTCCATGGCATTGGTGAGGGCCACGGGGTTGCCTGGT

GCCAGCGGGGATGGGTATTAGAGCCAGCTGAGTCCTCAGGCCTGTGTTT

CTGCTCCACCCTAGCGAGTCCATGCTACCCAGCCCAGGTGTATGGGCTGG

ACCGGCGCTTCTGGAGGAAGTACCTACACCTGGACTTTCATGCCCTGATG

CACCTAGCTACAGAAGAGCTCCTGCTGAGAGGCCGATGACCACCTTACAT

GGGAGGGTGCCACATGATTGAGGCATGAGGCAAGCC-3' (584 bp).
```

The results were shown in FIG. 4.

The ES cell clone of the wild-type mouse (Recql4 +/+) (i.e., the gene whose exon 13 of RecQL4 is not deficient in both two chromosomes) provides 8 kb band. The ES cell clone of the RECQL4 gene-deficient heterozygous mouse (Recql4 +/−), i.e., the ES cell clone of the mouse wherein exon 13 of RecQL4 was deleted in one chromosome by gene targeting, provides 6 kb and 8 kb bands. The ES cell clone of the RECQL4 gene-deficient homozygous mouse (Recql4 −/−) i.e., the ES cell clone of the mouse wherein exon 13 of RecQL4 was deficient in both two chromosomes, provides only 6 kb band. The ES cell clone of the RECQL4 gene-deficient heterozygous mouse (Recql4 +/−) was used for next step.

Preparation of Exon 13 of RECQL4 Gene-deficient Mouse

The Recql4 +/− ES cell clone was injected into blastocyst (morula) which was obtained by salpingectomy of C57BL/6JNrs pregnant mouse (a mouse strain which has black eyes and black hairs and stored in National Institute of Radiological Sciences) using a microinjector (Narishige) and a piezo-micromanipulator system (Prime Tech). The obtained blastocyst was introduced into womb of pseudopregnant surrogate mother mouse which was bred with vasoligated male mouse to prepare a chimeric mouse.

From the obtained chimeric mice, male mouse with over 80% of fur color derived from Recql4 +/– ES cell (agouti) was selected.

The selected male mouse was bred with C57BL/6 female mouse to prepare a F1 mouse wherein RecQL4 allele gene (Recql4–) was introduced into germline.

Genotyping of the F1 mouse was performed by means of PCR using DNA which was extracted through partial excision of mouse's tail and primers for Recql4 gene. The primers used in PCR were as follows:

```
                                        (SEQ ID NO.: 9)
mQ4-5 (+) 30
5'-CTCGTGGTCTCGCCTCTCCTGTCACTCATG-3'

(SEQ ID NO.: 10)
mQ4-6 (-) 30
5'-GCCCACCATGGACAGGCAGGTGCGGAGGAG-3'

(SEQ ID NO.: 11)
pgkNeo5'-1(-) 30
5'-CTTGGGAAAAGCGCCTCCCCTACCCGGTAG-3'
```

The genotyped RECQL4 gene-deficient heterozygous mouse (Recql4 +/–) was intercrossed to produce RECQL4 gene-deficient homozygous mouse (Recql4 –/–), or were crossed with C57BL/6 to produce RECQL4 gene-deficient homozygous mouse (Recql4 –/–).

Varidation of Deleted Portion by Sequencing of Recgl4 Gene Transcript

For each of the wild-type (Recql4 +/+) mouse and the RECQL4 gene-deficient homozygous mouse (Recql4 –/–), total RNA was prepared from the primary mouse embryonic fibroblast (MEF) of embryo at embryonic day 14.5 and brain, heart, thymus, kidney and testis from adult mouse in accordance with common procedures. For the prepared total RNAs, RT-PCR of Recql4 gene transcript was performed using the following primers (shown as arrowheads in FIG. 2):

```
                                        (SEQ ID NO.: 12)
mQ4-5 (+) 30
5'-CTCGTGGTCTCGCCTCTCCTGTCACTCATG-3'

(SEQ ID NO.: 13)
mQ4-8 (-) 30
5'-CAGCTGGGCACTGCCGCCAAGGCAATGCAG-3'
```

The length of mutant PCR products (transcripts) from MEFs and testis of the RECQL4 gene-deficient homozygous mouse (Recql4 –/–) were shorter than those of the wild-type mouse (Recql4 +/+).

The mutant PCR products were cloned into pGEM-T Easy (Promega) in accordance with the common procedures and their sequences were determined using the following primers:

```
5'-CTGCCTCTCTCAGTGGTCAC-3'      (SEQ ID NO.: 14)

5'-GACAGGCAGGTGCGGAGGAG-3'      (SEQ ID NO.: 15)
```

Comparing the determined sequences of the PCR products from the RECQL4 gene-deficient homozygous mouse with those of the wild-type mouse, it was found that the sequence which constituted exon 13 (180 bp) was completely deleted in the PCR products from the RECQL4 gene-deficient homozygous mouse (Recql4 –/–) (FIG. 5). The results indicate that, in the mouse which was prepared in accordance with the above targeting method, (1) Whole exon 13 of RECQL4 gene was deleted; and (2) As a result of splicing, 3' end of exon 12 was normally bounded to 5' end of exon 14 (i.e., the amino acid sequences of the downstream exons beginning at exon 14 were identical with the corresponding amino acid sequences of the wild-type mouse).

Test Example 1

Evaluation of Expression Level of the Exon 13-deleted Transcript in the RECQL4 Gene-deficient Homozygous Mouse (Recql4 –/–)

Using quantitative PCR, expression level of the mutant Recql4 transcript (the exon 13-deleted transcript) in the RECQL4 gene-deficient homozygous mouse (Recql4 –/–) was compared with that of the wild-type Recql4 transcript in the wild-type mouse (Recql4 +/+).

Using cDNA which were prepared from 1 micro gram of total RNA of the RECQL4 gene-deficient homozygous mouse as a standard, serial dilutions of cDNA were prepared from total RNA of the wild-type mouse testis (0 to 0.1 of the wild-type mouse to one of the RECQL4 gene-deficient homozygous mouse). PCR was performed using a mixture (as template) of the obtained serial dilutions of cDNA from the wild-type mouse and cDNA of the RECQL4 gene-deficient homozygous mouse, and primers sandwiching exon 13 which was deleted in the RECQL4 gene-deficient homozygous mouse as follows:

```
                                        (SEQ ID NO.: 16)
5'-CTCGTGGTCTCGCCTCTCCTGTCACTCATG-3'

(SEQ ID NO.: 17)
5'-CAGCTGGGCACTGCCGCCAAGGCAATGCAG-3'
```

The results are shown in FIG. 6. In FIG. 6, mix proportion values of each mixture were normalized by data which were obtained in RT-PCR using primer set specific to Gapdh gene. FIG. 6 indicates that the expression level of the mutant transcript in the RECQL4 gene-deficient homozygous mouse was 1 to 2% of the expression level of the wild-type transcript in the wild-type mouse.

Test Example 2

Growth Retardation (1) Evaluation Based on Survival Rate

Among the obtained RECQL4 gene-deficient homozygous mice (Recql4 –/–), approximately 40% of the mice died just after birth and 80% of the remaining mice died within 2 days after birth. Altogether, 95% of the mice died within 2 weeks after birth. However, 5% of the remaining mice were survived over 2 weeks after birth.

In order to determine embryonic lethality of the RECQL4 gene-deficient homozygous mouse (Recql4 –/–), the mouse which was obtained by caesarian section was subjected to genotyping. The result indicates that the ratio of the wild-type mouse (Recql4 +/+): RECQL4 gene-deficient heterozygous mouse (Recql4 +/–): RECQL4 gene-deficient homozygous mouse (Recql4 –/–) was 19:43:14, which was approximately consistent with the result derived from Mendel's law. Therefore, this result indicates that death at embryonic period was not due to the mutation of RECQL4 gene.

(2) Evaluation Based on Body Weight

The average body weight of the wild-type mouse (Recql4 +/+), the RECQL4 gene-deficient heterozygous mouse (Recql4 +/−) and the RECQL4 gene-deficient homozygous mouse (Recql4 −/−) at embryonic day 19 was 1.48±0.17 g, 1.51±0.21 g and 0.86±0.12 g, respectively. Therefore, the body weight of the RECQL4 gene-deficient homozygous mouse was approximately 60% of the body weight of the wild-type mouse (FIG. 7).

After that time, growth retardation of the RECQL4 gene-deficient homozygous mouse was continued. The body weight of the RECQL4 gene-deficient homozygous mouse at 10 weeks after birth was approximately one-third of the body weight of the wild-type mouse (FIG. 8).

(3) Evaluation Based on Cellular Proliferation

MEFs were isolated from the wild-type mouse (Recql4 +/+), the RECQL4 gene-deficient heterozygous mouse (Recql4 +/−) and the RECQL4 gene-deficient homozygous mouse (Recql4 −/−), respectively and the isolated MEFs were examined for their cell proliferation.

MEFs were isolated by removing head and guts from embryo at embryonic day 14.5, homogenating the obtained tissue and treating the obtained homogenate with trypsin. MEFs were cultured in Dulbecco's modified Eagle's medium (Sigma) supplemented with 10% fetal bovine serum, 50 micro U/ml of penicillin, 50 micro gram/ml of streptomycin and 58 micro M of 2-mercaptoethanol. MEFs culture on a 10 mm dish were incubated in an incubator which was maintained at 37 deg C. and 5% $CO_2$. $1.0 \times 10^5$ cells were plated onto a 60 mm dish in duplicate. The culture medium was changed everyday and cells were counted every 24 h using a Coulter counter (Beckman Coulter). The results are shown in FIG. 9. As compared to MEFs from the wild-type mouse (Recql4 +/+) and the RECQL4 gene-deficient heterozygous mouse (Recql4 +/−), MEFs from the RECQL4 gene-deficient homozygous mouse (Recql4 −/−) exhibited significantly low proliferation potency.

From the results above, it was found that the RECQL4 gene-deficient homozygous mouse (Recql4 −/−) exhibited growth retardation compared to the wild-type mouse (Recql4 +/+). Growth retardation is one of the characteristics of human RTS. Therefore, the mutant mouse of the present invention can be used for an animal model for human RTS.

Test Example 3

Skin Abnormalities (1) Evaluation Based on Appearance

The majority of the RECQL4 gene-deficient homozygous mice (Recql4 −/−) exhibited some skin abnormalities. Initially, hair loss was not noticeable. However, around 6 weeks after birth, hair loss was subsequently noted on the neck, back and the region from the root of the front leg to the lateral abdominal. During this period, some of the mutant mice also exhibited colorless hair on the rump and abdominal regions. Furthermore, the mouse whose hair loss lesions reached 20% of the whole body surface was observed.

At 2 to 3 months after birth, lesions with erosive bleeding on the hairless skin were observed. These lesions healed through crust formation, but without regrowth of hair. The lesions were often found in brittle skin areas which were frequently subjected to physical contact (for example, penis of male).

Dry skin was most remarkable in the tail and was found in 60% of the mutant mice at 3 to 4 months after birth.

(2) Histological Evaluation

In order to perform histological evaluation, mouse tissues were fixed in 10% buffered formalin, embedded in paraffin blocks and sectioned. Staining was performed with hematoxylin and eosin. The sections were microphotographed using a microscope, ECLIPSE TE300 (Nikon) with 40×, 100× and 400× magnification.

The mutant mouse exhibited hypoplasia of the epidermis, dermis and subcutaneous tissue compared to the wild-type mouse.

From the results above, it was found that RECQL4 gene-deficient homozygous mouse (Recql4 −/−) exhibited skin abnormalities compared to the wild-type mouse (Recql4 +/+). Skin abnormalities are one of the characteristics of human RTS. Therefore, the mutant mouse of the present invention can be used for an animal model for human RTS.

Test Example 4

Hypoplasia of Other Tissues

Bone tissue, small intestinal epithelium and lymphatic tissue were microphotographed in the same manner as used in Test Example 3.

As compared with the wild-type mouse, the RECQL4 gene-deficient homozygous mouse (Recql4 −/−) exhibited a decreased trabecula formation in osteogenetic layer.

Furthermore, the decreased size and number of villi in the small intestine were found in the RECQL4 gene-deficient homozygous mouse. Fewer dividing cells in the crypts and connective tissue were observed in the RECQL4 gene-deficient homozygous mouse. These findings suggest that the deletion of exon 13 of RECQL4 gene particularly affects the actively proliferating intestinal epithelium.

From the histological observation of lymphoid tissue, it was found that the size of thymi of the RECQL4 gene-deficient homozygous mouse (Recql4 −/−) was remarkably smaller than that of the wild-type mouse.

Furthermore, the number of thymi cells of the RECQL4 gene-deficient homozygous mouse (Recql4 −/−) was significantly smaller than that of the wild-type mouse (newborn wild-type mouse: $1 \times 10^7$ (n=1); newborn RECQL4 gene-deficient homozygous mouse: 0.6 to $5 \times 10^5$ (n=2); adult wild-type mouse: $2.0 \times 10^7$ (n=1); adult RECQL4 gene-deficient homozygous mouse: $1.3 \times 10^7$ (n=1)).

The cortical-medullary boundary in thymi of the RECQL4 gene-deficient homozygous mouse (Recql4 −/−) was unclear. Furthermore, the size and number of the white pulp of the RECQL4 gene-deficient homozygous mouse (Recql4 −/−) were significantly smaller than those of the wild-type mouse.

From the results above, it was found that the RECQL4 gene-deficient homozygous mouse (Recql4 −/−) exhibited osteogenesis abnormalities, abnormalities in small intestinal epithelium and abnormalities in lymphatic tissue. Osteogenesis abnormalities is one of the characteristics of human RTS. Therefore, the mutant mouse of the present invention can be used for an animal model for human RTS.

INDUSTRIAL APPLICABILITY

The present invention provide a RECQL4 gene-deficient homozygous animal (Recql4 −/−) which was considered to have a high lethality, especially a RECQL4 gene-deficient homozygous mouse (Recql4 −/−) and a preparation method thereof. The mouse of the present invention exhibits many characteristics of human RTS including growth retardation, skin abnormalities and osteogenesis abnormalities. Therefore, the mouse of the present invention can be used for an animal model for human RTS.

The invention claimed is:

1. A mouse having homozygous mutation of the endogenous RECQL4 gene, wherein the whole exon 13 of the wild-type RECQL4 gene is deleted, and the mouse exhibits colorless hair, hair loss, short stature, osteogenesis abnormalities, immunological abnormalities and sterility which are characteristic of Rothmund-Thomson syndrome.

2. The mouse according to claim 1, wherein exon 13 of RECQL4 gene has the sequence shown in SEQ ID NO:3.

3. The mouse according to claim 1, wherein RECQL4 loses a helicase activity.

4. A method for preparing the mouse according to claim 1 comprising the steps: Deleting exon 13 of endogenous RECQL4 gene in mouse embryonic stem (ES) cell by using homologous recombination;

Selecting ES cell containing the mutated RECQL4 allele;

Introducing the ES cell into a blastocyst;

Implanting the blastocyst into a psuedopregnant mouse, wherein the resultant mouse gives birth to a chimeric mouse; and breeding the chimeric mouse to obtain the mouse according to claim 1.

5. The method according to claim 4, wherein exon 13 of RECQL4 gene has the sequence shown in SEQ ID NO.:3.

6. The method according to claim 4, wherein RECQL4 loses a helicase activity.

* * * * *